US009737889B2

(12) United States Patent
Moon et al.

(10) Patent No.: US 9,737,889 B2
(45) Date of Patent: Aug. 22, 2017

(54) MICROFLUIDIC APPARATUS

(71) Applicant: Samsung Electronics Co., Ltd., Suwon-si, Gyeonggi-do (KR)

(72) Inventors: Hui-sung Moon, Yongin-si (KR); Min-Seok S. Kim, Yongin-si (KR); Jong-myeon Park, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 624 days.

(21) Appl. No.: 14/273,697

(22) Filed: May 9, 2014

(65) Prior Publication Data

US 2015/0064774 A1 Mar. 5, 2015

(30) Foreign Application Priority Data

Sep. 4, 2013 (KR) ........................ 10-2013-0106310

(51) Int. Cl.
*G01N 33/00* (2006.01)
*B01L 3/00* (2006.01)

(52) U.S. Cl.
CPC ..... *B01L 3/502738* (2013.01); *B01L 3/50273* (2013.01); *B01L 2200/0621* (2013.01); *B01L 2300/0803* (2013.01); *B01L 2300/087* (2013.01); *B01L 2300/0864* (2013.01); *B01L 2400/0409* (2013.01); *B01L 2400/0677* (2013.01)

(58) Field of Classification Search
CPC ......... B01L 3/502738; B01L 2300/087; B01L 2200/0621
See application file for complete search history.

(56) References Cited

U.S. PATENT DOCUMENTS 6,063,589 A * 5/2000 Kellogg .............. B01F 13/0059 366/DIG. 3
2008/0226504 A1 9/2008 Park et al.

FOREIGN PATENT DOCUMENTS

JP 2006-145451 B2 6/2006
JP 2011-058956 B2 3/2011
KR 2011/0058089 A 1/2013
KR 2013-0000009 A 1/2013

OTHER PUBLICATIONS

Translation of JP 2006-145451.*

* cited by examiner

*Primary Examiner* — Sam P Siefke
(74) *Attorney, Agent, or Firm* — Leydig, Voit & Mayer, Ltd.

(57) ABSTRACT

A microfluidic apparatus mounted on a rotation driving unit for inducing a fluid to flow due to a centrifugal force includes: a target chamber that houses a first fluid; a first chamber that houses a second fluid and is disposed closer to a rotation center of the microfluidic apparatus in a radius direction than the target chamber, the first chamber being connected to the target chamber by a first channel; a first valve that prevents a flow of the second fluid through the first channel; and a second chamber disposed closer to the rotation center in the radius direction than the target chamber and connected to the target chamber by a second channel, wherein the first fluid is transported to the second chamber by supplying the second fluid to the target chamber by the centrifugal force.

15 Claims, 9 Drawing Sheets

MICROFLUIDIC APPARATUS

RELATED APPLICATION

This application claims the benefit of Korean Patent Application No. 10-2013-0106310, filed on Sep. 4, 2013, in the Korean Intellectual Property Office, the entire disclosure of which is hereby incorporated by reference.

BACKGROUND

1. Field

The present disclosure relates to a disc-based microfluidic apparatus which may transport a fluid in an opposite direction of a centrifugal force.

2. Description of the Related Art

A lab-on-a-disc-based microfluidic apparatus, which controls a fluid based on a centrifugal force, is an apparatus that may automatically perform a series of processes with respect to various samples. The microfluidic apparatus is used in diverse fields to analyze biological samples, extract target materials from biological samples, perform biochemical process on different samples, etc.

The microfluidic apparatus may transport a fluid only in a direction of the centrifugal force. When the microfluidic apparatus is rotated, the fluid housed in the microfluidic apparatus has a higher potential energy as the fluid is closer to a rotation center and has a lower potential energy as the fluid is farther from the rotation center. That is because the fluid may flow only from a position having a higher potential energy to a position having a lower potential energy. Thus, as there are more processes to be performed via the microfluidic apparatus on the samples, a radius (a distance in the direction of the centrifugal force) of the microfluidic apparatus increases, thereby leading to an increase in the size of the microfluidic apparatus. In this case, the size of a driving device for rotation driving the microfluidic apparatus should also increase.

SUMMARY

Provided is a microfluidic apparatus that may transport a sample located close to an outer circumference thereof back to an inner circumference thereof.

According to an aspect of the present invention, a microfluidic apparatus inducing a fluid to flow due to a centrifugal force includes: a target chamber housing a first fluid; a first chamber that houses a second fluid, is disposed farther inside than the target chamber in a radius direction, and is connected to the target chamber by a first channel; a first valve that controls a flow of the second fluid through the first channel; and a second chamber that is disposed farther inside than the target chamber in the radius direction and is connected to the target chamber by a second channel, wherein the first fluid is transported to the second chamber by supplying the second fluid to the target chamber by a centrifugal force.

The microfluidic apparatus may further include a second valve that controls the flow of the fluid through the second channel.

The first fluid and the second fluid are typically not mixed with each other.

The first channel may be filled with a gas.

The microfluidic apparatus may include a first processing unit that processes a sample and supplies the first fluid including a target material to the target chamber, and the second fluid may include a waste fluid that is separated from the sample and discharged from the sample processing unit.

The microfluidic apparatus may further include a second processing unit that is disposed in an outer portion of the second chamber and receives the first fluid from the second chamber.

According to another aspect of the present invention, a microfluidic apparatus inducing a fluid to flow due to a centrifugal force includes: a first processing unit for separating a target cell from a sample; a target chamber that is disposed in an outer portion of the first processing unit and receives a first fluid including the target cell from the first processing unit; a first chamber that houses a second fluid, is disposed farther inside than the target chamber, and is connected to the target chamber by a first channel; a second chamber that is disposed farther inside than the target chamber and is connected to the first chamber by a second channel; and a second processing unit that is disposed in an outer portion of the second chamber and is connected to the second chamber, wherein the first fluid is transported to the second chamber by supplying the second fluid to the target chamber by a centrifugal force.

The microfluidic apparatus may further include a first valve that controls a flow of the fluid through the first channel. The microfluidic apparatus may further include a second valve that controls a flow of the fluid through the second channel.

The first fluid and the second fluid are typically not mixed with each other.

The first channel may be filled with a gas.

The first processing unit may include a sample chamber in which a complex in which fine beads are bound to the target cell in the sample is formed; and a separation chamber that separates the complex from the sample using a density gradient medium with a density lower than that of the complex and higher than that of other materials in the sample and provides the first fluid including the complex to the target chamber.

The first chamber is connected to the sample chamber, and an upper material layer above the target cell in the sample chamber may be discharged from the sample chamber to the first chamber.

The second processing unit may receive the first fluid from the second chamber.

The target cell may be a circulating tumor cell, a cancer stem cell, or a cancer cell.

BRIEF DESCRIPTION OF THE DRAWINGS

These and/or other aspects will become apparent and more readily appreciated from the following description of the embodiments taken in conjunction with the accompanying drawings, in which.

DETAILED DESCRIPTION

Reference will now be made in detail to embodiments, examples of which are illustrated in the accompanying drawings. In this regard, the present embodiments may have different forms and should not be construed as being limited to the descriptions set forth herein. Accordingly, the embodiments are merely described below, by referring to the figures, to explain aspects of the present description.

Figure 1:
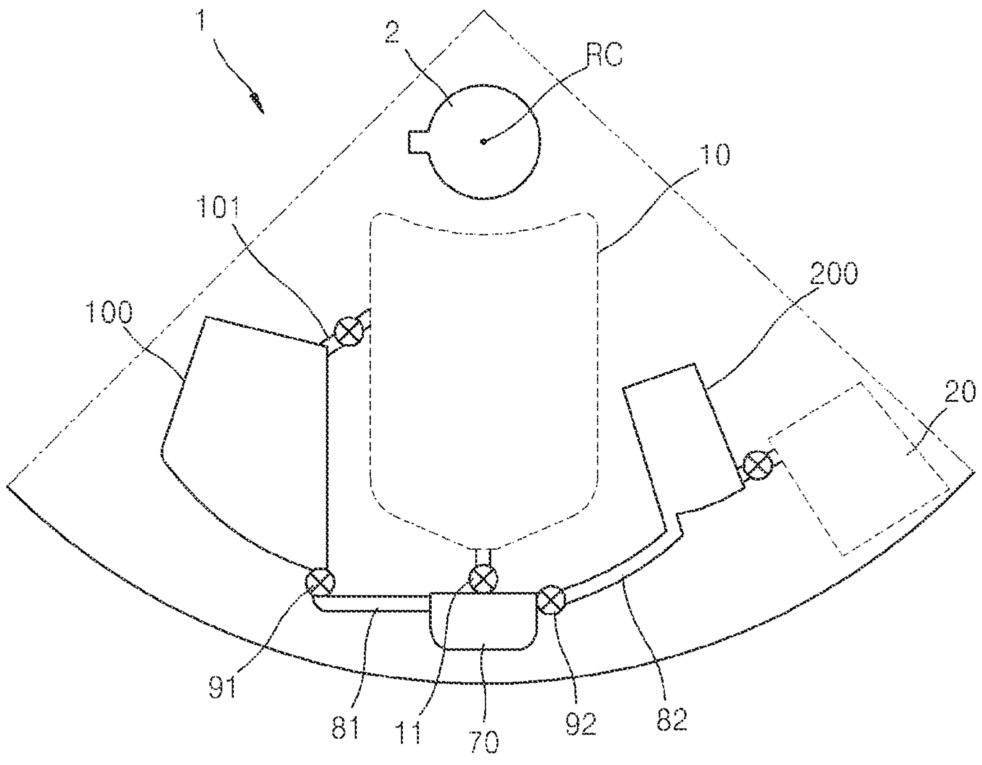
FIG. 1 is a schematic diagram of a microfluidic apparatus.

FIG. 1 is a schematic diagram of a microfluidic apparatus 1 according to an embodiment of the present invention. The microfluidic apparatus 1 includes a microfluidic structure including a chamber for housing a fluid and a channel for permitting passage of the fluid. The microfluidic apparatus 1 may, for example, have a rotatable disc shape. FIG. 1 illustrates only a portion of the microfluidic apparatus 1. The microfluidic apparatus 1 may include a bottom structure, including a concaved microfluidic structure including chambers providing a space for housing the fluid and a channel for permitting passage of the fluid between each of the chambers, and a top structure (a top plate) that is combined with the bottom structure and forms a top wall of the microfluidic structure. The microfluidic apparatus 1 may have a double-plate structure having a top plate, and a bottom plate including the microfluidic structure. Alternatively, the microfluidic apparatus 1 may have a triple-plate structure including a top plate, a bottom plate, and a partition plate defining a microfluidic structure, the partition plate being interposed between the top plate and the bottom plate. The plates may be combined using an adhesive or a double-sided adhesive tape, or by ultrasonic wave fusing or laser fusing.

The microfluidic apparatus 1 may be formed of a plastic material that is moldable and has a biologically inactive surface. Examples of such a plastic material are acryl and PDMS. However, the material for the microfluidic apparatus 1 is not limited thereto, and may be any one of various materials that have chemical and biological stabilities, optical transparency, and mechanical processability.

The microfluidic apparatus 1 is mounted on a rotation driving unit (not shown) that provides a centrifugal force upon rotation of the microfluidic apparatus 1. To this end, a mounting portion 2 is provided at a rotation center RC of the microfluidic apparatus 1 to be combined with the rotation driving unit. The fluid in the microfluidic apparatus 1 goes through desired processing steps while being sequentially transported from a location close to the rotation center RC to a location farther from the rotation center RC. Hereinafter, "an inner portion" refers to a location close to the rotation center RC in a radius direction of the microfluidic apparatus 1, and "an outer portion" refers to a location farther from the rotation center RC in the radius direction of the microfluidic apparatus 1.

For example, referring to FIG. 1, while a sample goes through predetermined processing steps in a first processing unit 10, a first fluid discharged from the first processing unit 10 is housed in a target chamber 70. The first processing unit 10 may separate a target material, for example a specific target cell, from a biological sample. In this case, the first fluid may be a fluid including the target cell. The structure of the first processing unit 10 may vary according to sample processing types, and thus, the first processing unit 10 illustrated in FIG. 1 is only an example. Along the radius direction from the rotation center RC (a direction of a centrifugal force), the target chamber 70 is disposed in an outer portion of the microfluidic apparatus 1. A valve 11 controls flow of the fluid between the first processing unit 10 and the target chamber 70. For example, the valve 11 may be a normally open valve that may be converted from an open state for permitting fluid flow to a closed state for blocking fluid flow after the fluid flows from the first processing unit 10 to the target chamber 70.

Regarding the microfluidic apparatus 1, to perform a series of sequential processes including, for example, separating the target cell from the first fluid using the first fluid housed in the target chamber 70, a second processing unit 20 including a microfluidic structure for the sequential processes is disposed in an outer portion of the microfluidic apparatus 1 in the radius direction. To this end, the radius of the microfluidic apparatus 1 increases.

As a method of performing the sequential processes in the microfluidic apparatus 1 without increasing a size thereof, the second processing unit 20 may be disposed closer to the rotation center RC than the target chamber 70, and the first fluid may be extracted from the target chamber 70 and loaded into the second processing unit 20 using an instrument such as a pipette. In this case, an advantage of the lab-on-a-disc-based microfluidic apparatus 1 in regard to automation of a series of processes may disappear.

According to the microfluidic apparatus 1 of the present embodiment, a potential energy of the fluid is increased by a centrifugal force. That is, using centrifugal force, the first fluid housed in the target chamber 70 is transported to a second chamber 200 that is closer to the rotation center RC in the radius direction than the target chamber 70, wherein the second chamber 200 has a higher potential energy than the target chamber 70. According to such a structure, while maintaining the advantage of the microfluidic apparatus 1 based on a lab-on-a-disc, that is, a series of automated processes, multiple processing steps may be sequentially performed in the identical microfluidic apparatus 1.

Referring to FIG. 1, a first chamber 100 and the second chamber 200 are illustrated. The first chamber 100 houses a second fluid. The second chamber 200 has a higher potential energy than the target chamber 70. That is, the second chamber 200 is disposed in an inner portion of the microfluidic apparatus 1. The first chamber 100 has a higher potential energy than the second chamber 200. The second fluid may, for example, be a buffer solution. The first chamber 100 is connected to the target chamber 70 by a first channel 81. A first valve 91 controls the flow of the fluid in the first channel 81. The second chamber 200 is connected to the target chamber 70 by a second channel 82. The second channel 82 may include a second valve 92 for controlling the flow of the fluid. The first and second valves 91 and 92 may be normally closed valves that may change the first and second channels 81 and 82 from a closed state to an open state. Alternatively, the second valve 92 may be a normally open valve that may change the second channel 82 from an open state to a closed state.

Figure 2:
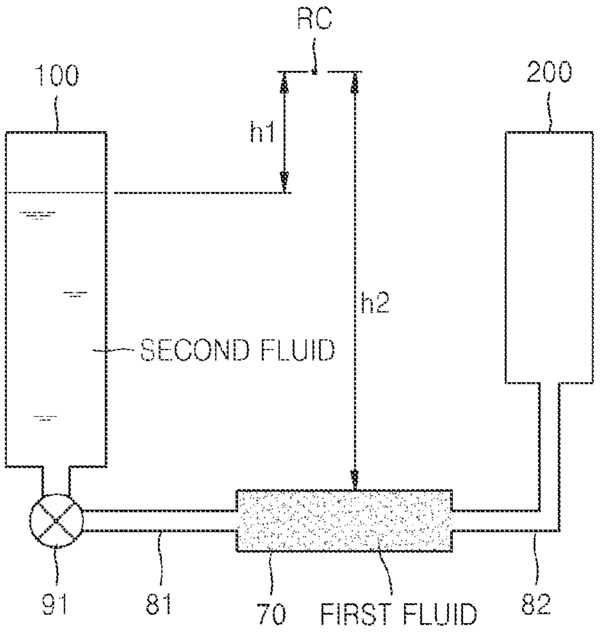
FIG. 2 schematically illustrates a first chamber, a second chamber, a target chamber, a first channel, and a second channel of FIG. 1 in a state where the first channel is closed.

FIG. 2 is a schematic illustration of the first and second chambers 100 and 200, the target chamber 70, and the first and second channels 81 and 82 of FIG. 1. FIG. 2 illustrates a closed state of the first channel 81. Referring to FIG. 2, the target chamber 70 houses the first fluid, and the first chamber 100 houses the second fluid. The second chamber 200 is empty. Thus, from the rotation center RC, a fluid level of the second fluid in the first chamber 100 h1 is higher than a fluid level of the first fluid in the target chamber 70 h2. In the microfluidic apparatus 1, based on a centrifugal force a potential energy is higher as it is closer to the rotation center RC. Therefore, the second fluid has a higher potential energy than the first fluid.

To transport the first fluid to the second chamber 200, the first valve 91 is driven to open the first channel 81. When the microfluidic apparatus 1 is rotated, the second fluid flows into the target chamber 70 through the first channel 81 due to a centrifugal force. The first fluid in the target chamber 70 is transported to the second chamber 200 through the second channel 82 by being pushed by the second fluid. If the microfluidic apparatus 1 continues to rotate, the first and second fluids in the first and second chambers 100 and 200, the target chamber 70, and the first and second channels 81 and 82 will reach an equilibrium state.

Figure 3:
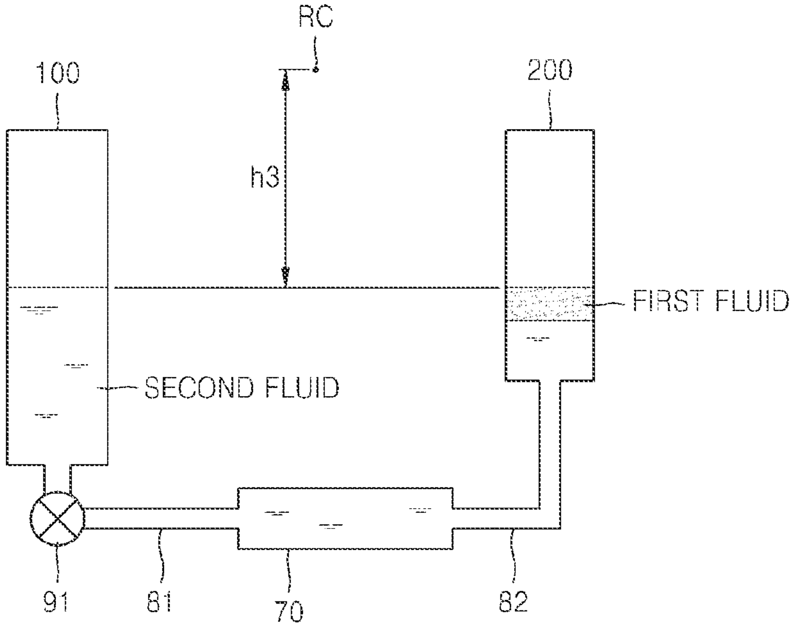
FIG. 3 schematically illustrates a first chamber, a second chamber, a target chamber, a first channel, and a second channel of FIG. 1 in an equilibrium state.

FIG. 3 is a schematic illustration of an equilibrium state of the first and second chambers 100 and 200, the target chamber 70, and the first and second channels 81 and 82 of FIG. 1. Referring to FIG. 3, in the equilibrium state, the fluid levels of the fluids in the first chamber 100 and the second chamber 200 are both equal to h3, and the fluid level of the first fluid is decreased from h2 to h3.

An amount of the second fluid housed in the first chamber 100 may be determined such that the first fluid may be completely transported to the second chamber 200 in an equilibrium state. That is, the amount of the second fluid housed in the first chamber 100 is the same as or higher than an amount whereby the fluid level of the first fluid in the second chamber 200 and the fluid level of the second fluid in the first chamber 100 are the same, and thus, the first and second chambers 100 and 200 reach an equilibrium state after the first fluid fills the first channel 81, the target chamber 70, and the second channel 82. The first fluid is then completely transported to the second chamber 200.

As described above, according to the microfluidic apparatus 1 according to the present embodiment, the first fluid may be transported in an opposite direction of the centrifugal force, using a centrifugal force generated by a rotation of the microfluidic apparatus 1. Thus, a space according to a difference in the fluid level of the first fluid in an outer portion of the microfluidic apparatus 1, that is, a space according to the difference between h3 and h2, may be obtained. Therefore, by disposing the second processing unit 20 for performing the sequential processes in the obtained space, the second processing unit 20 may be integrated in the microfluidic apparatus 1 without increasing the radius of the microfluidic apparatus 1.

Figure 4:
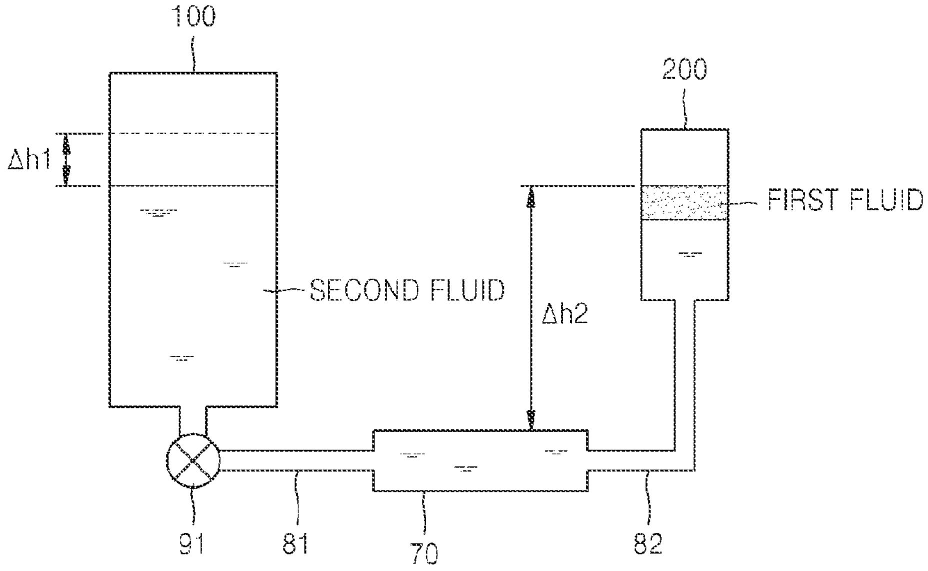
FIG. 4 schematically illustrates a first chamber, a second chamber, a target chamber, a first channel, and a second channel of FIG. 1, wherein a cross-sectional area of the first chamber is greater than that of the second chamber.
Figure 5:
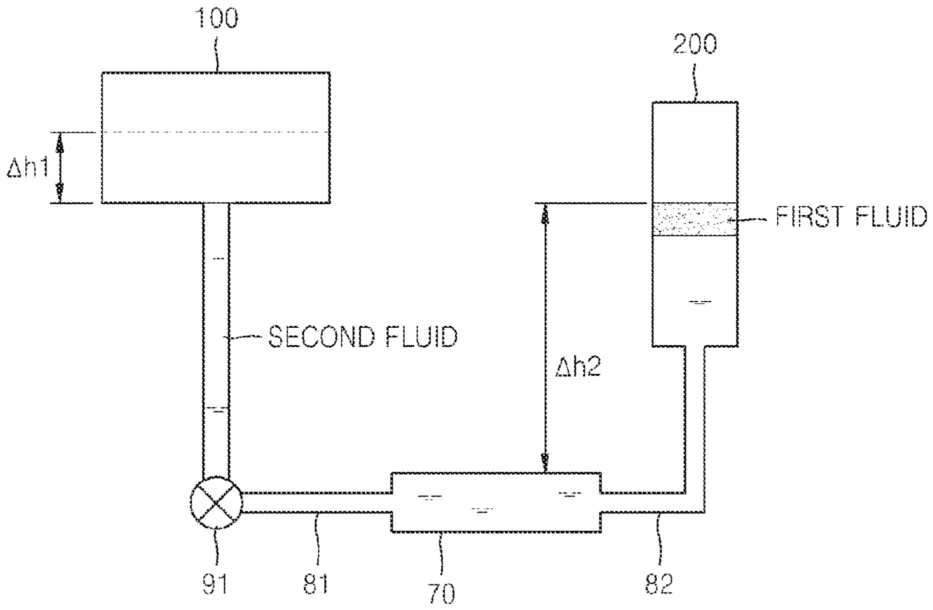
FIG. 5 schematically illustrates a first chamber, a second chamber, a target chamber, a first channel, and a second channel of FIG. 1, wherein a cross-sectional area of a portion of the first chamber close to a rotation center of the microfluidic apparatus is greater than that of the other portion of the first chamber that is far from the rotation center of the microfluidic apparatus.

As illustrated in FIG. 4, the microfluidic apparatus 1 may be formed such that a cross-sectional area of the first chamber 100 is greater than that of the second chamber 200. According to such a structure, a fluid level change Δh2 of the first fluid that is greater than a fluid level change Δh1 of the second fluid may be obtained. Also, as long as the fluid level change Δh2 of the first fluid may be obtained, the cross-sectional area of the first chamber 100 should not necessarily be uniform in the radius direction, and thus, as illustrated in FIG. 5, the first chamber 100 may be formed such that a cross-sectional area of a portion close to the rotation center RC is greater than that of the other portion farther from the rotation center RC. By implementing the first chamber 100 having such a shape, a degree of freedom for disposing other microfluidic structures in the microfluidic apparatus 1 may be improved.

The second fluid may be a fluid having an affinity with the first fluid. In this case, the first fluid and the second fluid may be mixed with each other in the second chamber 200. The second fluid may be a fluid that will not mix with the first fluid (i.e., the two fluids may be immiscible). To this end, the second fluid may be a fluid having a large difference in a surface energy from the first fluid. Alternatively, the second fluid may be a fluid having a different density from that of the first fluid. For example, if the first fluid is water, oil may be implemented as the second fluid. In this case, as illustrated in FIGS. 3 through 5, the first fluid and the second fluid are not mixed with each other and remain as separated layers in the second chamber 200. Thus, when performing sequential processes, the first fluid may be easily extracted.

Figure 6:
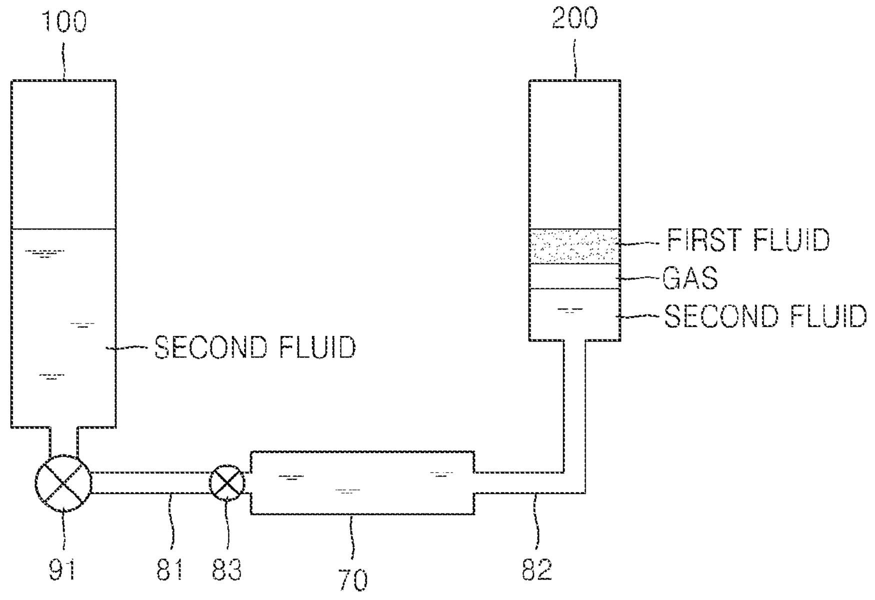
FIG. 6 schematically illustrates a first chamber, a second chamber, a target chamber, a first channel, and a second channel of FIG. 1 in a state in which a first fluid and a second fluid are separated by a gas in the second chamber.

To maintain the first and second fluids as separate layers in the second chamber 200, the first channel 81 may be filled with a gas. In this case, as illustrated in FIG. 6, a third valve 83 may be provided in a portion of the first channel 81 that is close to the target chamber 70. The third valve 83 may be a normally closed valve. According to such a structure, when the first and third valves 91 and 83 are open and a centrifugal force is applied to the second fluid, the gas and the first fluid are transported to the second chamber 200 by being pushed by the second fluid. Also, the first fluid and the second fluid may remain as separate layers due to the gas interposed therebetween. That is, while an interface between the fluid and the gas is maintained by the gas trapped between the first fluid and the second fluid, the gas may be transported to the second chamber 200 and remain in the interposed state between the first fluid and the second fluid. The gas may include air, nitrogen (N), and an inert gas.

The first chamber 100 may be a waste chamber for housing a waste fluid discharged from the first processing unit 10. Referring to FIG. 1, the first chamber 100 may be connected to the first processing unit 10 by a waste channel 101. For example, after centrifuging of a sample is performed in the first processing unit 10, an upper material layer may be discharged. Such a waste fluid may be housed in the first chamber 100 through the waste channel 101 and used as the second fluid. If an amount of the waste fluid is sufficiently large, there is no need to additionally fill the second fluid in the first chamber 100, and the waste fluid discharged from the process of the first processing unit 10 may be used as the second fluid. If the amount of waste fluid is not sufficiently large, the second fluid may be supplemented in the first chamber 100. According to such a structure, the amount of use of the second fluid may be reduced or nullified.

Hereinafter, the microfluidic apparatus 1 for separating a target cell from a sample, according to an embodiment of the present invention, will be described.

Figure 7:
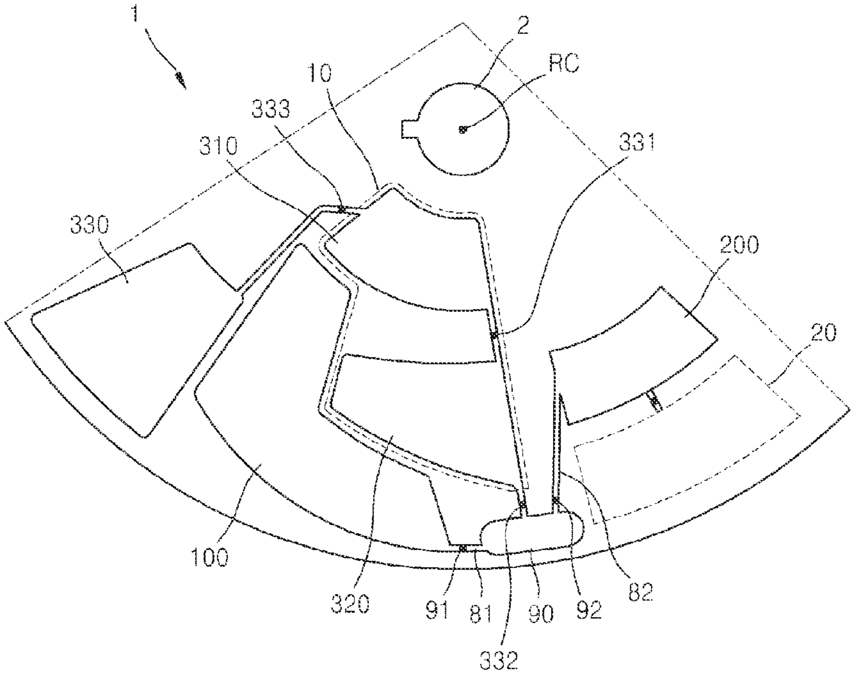
FIG. 7 is a plan view of a microfluidic apparatus for separating a target cell.

FIG. 7 is a plan view of the microfluidic apparatus 1 for separating the target cell, according to an embodiment of the present invention. A first processing unit 10 of the microfluidic apparatus 1 separates a target cell from a biological sample based on a density difference, and provides a first fluid including the target cell to a target chamber 70. The first fluid is transported to a second processing unit 20 and sequentially processed. The structure of the second processing unit 20 may vary according to types of the sequential processes, and thus, a detailed structure of the second processing unit 20 is omitted in FIG. 7.

According to the present embodiment, the first processing unit 10 includes a sample chamber 310 and a separation chamber 320. The sample chamber 310 provides a fluid including a target cell-fine beads complex. In the sample chamber 310, the target cell included in the sample contacts fine beads, and a complex in which the fine beads are bound to the target cell is formed. The fine beads may, for example, be solid micro beads, magnetic beads, gel beads, and/or polymer micro beads.

The target cell may be a circulating tumor cell (CTC), a cancer stem cell, or a cancer cell. The target cell may, for example, be a cancer or tumor cell selected from the group consisting of bladder cancer, breast cancer, uterine cervical cancer, cholangiocarcinoma, colorectal cancer, uterine endometrial cancer, esophageal cancer, stomach cancer, head and neck cancer, kidney cancer, liver cancer, lung cancer, nasopharyngeal cancer, ovarian cancer, pancreas cancer, gallbladder carcinoma, prostate cancer, thyroid cancer, osteosarcoma, rhabdomyosarcoma, synovial sarcoma, Kaposi's sarcoma, leiomyosarcoma, malignant fibrous histicytoma, fibrosarcoma, adult T-cell leukemia, lymphoma, multiple myeloma, glioblastoma/astrocytoma, melanoma mesothelioma, and Wilms' tumor.

A sample may be any one of various biological samples as long as the target cell may exist therein. For example, the biological sample may be selected from the group consisting of a biopsy sample, a tissue sample, a cell suspension in which a separated cell is suspended in a liquid medium, a cell culture, and a combination thereof. The biological sample may be selected from the group consisting of blood, bone marrow, saliva, lachrymal fluid, urine, semen, mucous fluid, and a combination thereof. For example, blood may be used as a sample to separate CTCs.

A ligand that is specific to a surface marker of a target cell may bind to fine beads. The fine beads may bind to the target cell to increase the density of the target cell. The fine beads may have a density that may cause a difference between the density of the target material in a sample and the density of the remaining cells other than the target cell. For example, when blood containing a cancer cell as a target cell is used as a biological sample, since densities of a white blood cell and a red blood cell are respectively about 1.07 g/cm3 and about 1.1 g/cm3, fine beads with an appropriate density may be selected in consideration of such densities. The fine beads may be, for example, selected from the group consisting of polystyrene particles, polymethylmetaacrylate particles, latex particles, acrylonitril-butadiene-styrene copolymer (ABS) particles, a cyclic olefin copolymer particles, a melamine particles, and a complex thereof, but may not be limited thereto. A diameter of the fine beads may vary according to a target cell to be separated and fine beads to be used, and may be, for example, in a range of about 1 nm to about 100 μm, or about 10 nm to about 10 μm. The fine beads may be nano beads or micro beads.

The surface marker may be selected from the group consisting of a protein, sugar, lipid, a nucleic acid, and a combination thereof. For example, the surface marker may be a protein that is specifically expressed in cancer or tumor cells and is displayed on a cell membrane, and for example, may be EpCAM, c-Met, cytokeratines, CD45, Her2, or a combination thereof. In addition, the ligand that is specific to the surface marker may be an antibody that specifically connects to an antigen protein.

The separation chamber 320 is connected to the sample chamber 310. To make a fluid flow from the sample chamber 310 to the separation chamber 320 due to a centrifugal force, the separation chamber 320 is disposed in an outer portion of the microfluidic apparatus 1 in a radius direction from a rotation center RC. A sample valve 331 for controlling the flow of the fluid is between the separation chamber 320 and the sample chamber 310. The sample valve 331 may be a normally closed valve that is convertible from a state of blocking the flow of the fluid to a state of permitting the flow of the fluid.

The separation chamber 320 houses a density gradient medium (DGM). The DGM is provided to separate the complex from the sample based on a density gradient. The DGM has a density that is lower than that of the complex and higher than that of other fluids than the complex. In the separation chamber 320, the complex and the fluid are separated from each other with the DGM interposed therebetween. The complex gathers in the bottommost layer of the separation chamber 320, that is, in an outermost portion in the radius direction from the rotation center RC.

The target chamber 70 is disposed in an outer portion of the microfluidic apparatus 1 in the radius direction from the rotation center RC. Between the separation chamber 320 and the target chamber 70, a separation valve 332 for controlling the flow of the fluid is disposed. The separation valve 332 may be a normally open valve that may be converted from a state of permitting the fluid flow to a state of blocking the fluid flow. In the separation chamber 320, the complex gathers in the bottommost layer and is transported to the target chamber 70 due to a centrifugal force.

The first processing unit 10 may further include a waste chamber 330 for housing a waste fluid discharged from the sample chamber 310. The waste chamber 330 is disposed in an outer portion of the microfluidic apparatus 1 in the radius direction from the rotation center RC. A discharge valve 333 controls the flow of the fluid between the sample chamber 310 and the waste chamber 330. The discharge valve 333 may be a normally closed valve that may be converted from a state of blocking the fluid flow to a state of permitting the fluid flow. Alternatively, the discharge valve 333 may be a combination of the normally closed valve that may be changed from the blocking state to the opening state and the normally open valve that may be converted from the opening state to the blocking state. According to the combination, the discharge valve 333 is maintained in the closed state in a centrifugal process in the sample chamber 310, is changed to the open state during discharging of the waste fluid, and again is changed to the closed state after the discharging of the waste fluid is completed.

A portion of a sample in the sample chamber 310 may be removed before forming a complex in the sample chamber 310. For example, by centrifuging the sample in the sample chamber 310, an upper material layer located above the target cell may be discharged to the waste chamber 330. Then, the complex may be formed by combining the target cell and the fine beads by mixing fine beads and the sample. For example, when blood containing circulating tumor cells is centrifuged in the sample chamber 310, a plasma layer is located in the uppermost layer, that is, the layer closest to the rotation center RC. The plasma layer may be discharged to the waste chamber 330. A protein contained in the plasma layer may decrease a binding rate of the circulating tumor cell and the fine beads by combining with the fine beads. Thus, by removing the plasma layer, a binding efficiency of the fine beads and the circulating tumor cell may be increased.

The microfluidic apparatus 1 according to the present embodiment transports the first fluid including the complex gathering in the target chamber 70 to the second chamber 200 having a higher potential energy than the target chamber 70 by using a centrifugal force. To this end, the first chamber 100 housing the second fluid is provided. The first chamber 100 has a higher potential energy than the target chamber 70. Location relationships of the target chamber 70, the first chamber 100, and the second chamber 200, the first and second channels 81 and 82 connecting the above three, and the first and second valves 91 and 92 that controls the flow of the fluid through the first and second channels 81 and 82, are the same as illustrated in FIGS. 1 through 6. Thus, descriptions will be omitted.

Figure 8:
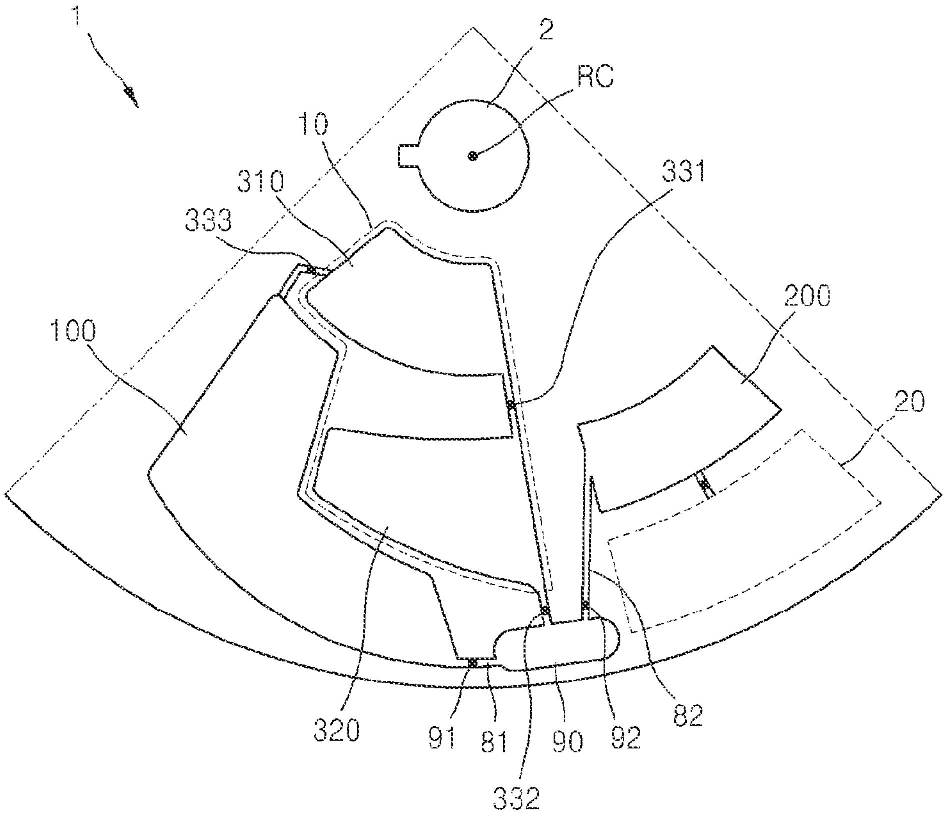
FIG. 8 is a plan view of a microfluidic apparatus for separating a target cell.

FIG. 8 is a plan view of the microfluidic apparatus 1 used for separating a target cell, according to another embodiment of the present invention. According to the microfluidic apparatus 1 illustrated in FIG. 8, the first chamber 100 and the waste chamber 330 are not separately provided, and a waste fluid discharged from the sample chamber 310 flows to the first chamber 100. Thus, the first chamber 100 functions as the waste chamber 330. In addition, the waste fluid is used as the second fluid. In other words, according to the embodiment illustrated in FIG. 8, the first chamber 100 is not separately provided, and the waste chamber 330 may function as the first chamber 100 for housing the second fluid. For example, when separating a circulating tumor cell from blood, even if plasma discharged from the sample chamber 310 contacts the complex in the target chamber 70, the plasma does not prevent the forming of the complex. Since an amount of plasma may be predicted from an amount of a sample (for example, blood) housed in the sample chamber 310, if the amount of plasma is greater than a required amount of the second fluid, the plasma may be used as the second fluid. If the amount of plasma is smaller than the required amount of the second fluid, the second fluid may be supplemented in advance in the first chamber 100 (or the waste chamber 330).

Figure 9A:
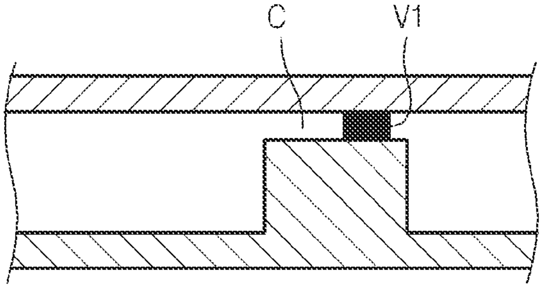
FIGS. 9A and 9B are cross-sectional views illustrating an example of a normally closed valve.
Figure 9B:
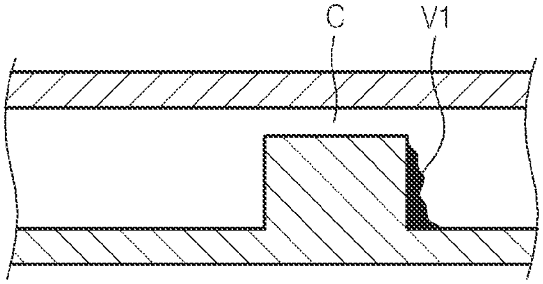

A microfluidic valve may be used as the normally closed valve or the normally open valve described above. FIGS. 9A and 9B are cross-sectional views illustrating an example of the normally closed valve. The normally closed valve may include a valve material V1 that is in a solid state at room temperature and thus clogs a channel C as illustrated in FIG. 9A. The valve material V1 melts at a high temperature by receiving energy from the outside and moves within the channel C, and as illustrated in FIG. 9B, the valve material V1 returns to a solid state when the channel C is opened.

Figure 10A:
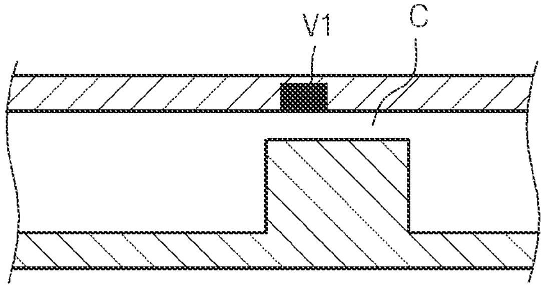
FIGS. 10A, 10B, and 10C are cross-sectional views illustrating examples of a normally open valve and an open/close valve.
Figure 10B:
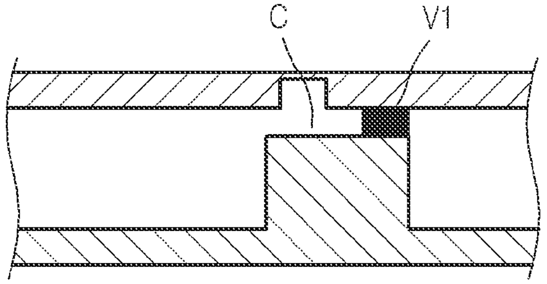
Figure 10C:
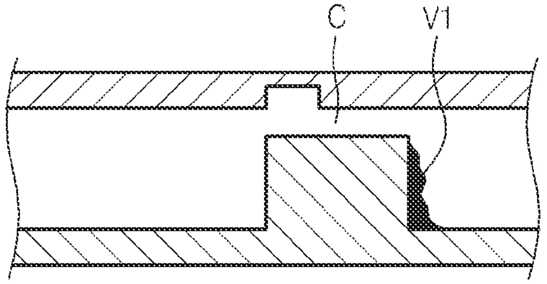

FIGS. 10A, 10B, and 10C are cross-sectional views illustrating examples of a normally open valve and an open/close valve. The normally open valve may include a valve material V1 that is in a solid state at room temperature. The valve material V1 exists above the channel C in a solid state, and thus, the channel C is maintained in an open state, as illustrated in FIG. 10A. The valve material V1 melts at a high temperature by receiving energy from the outside, moves within the channel C and coagulates, and thus, as illustrated in FIG. 10B, closes the channel C. Thus, the normally open valve may be embodied.

The valve material V1 in FIG. 10B melts at a high temperature by receiving energy from the outside and is discharged from the channel C. As illustrated in FIG. 10C, the valve material V1 returns to a solid state when the channel C is opened. Accordingly, an open/close valve may be embodied as illustrated in FIGS. 10A, 10B, and 100.

The energy transmitted from the outside may be, for example, an electromagnetic wave, and an energy source may be a laser beam source that generates a laser beam, a light emitting diode that generates visible light or infrared light, or an Xenon lamp. When a laser beam source is used, the laser beam source may include at least one laser diode. An external energy source may be selected according to a wavelength of an electromagnetic wave that is absorbable by exthothermic particles included in the valve material V1. As a valve material V1, a thermoplastic resin, such as a cyclic olefin copolymer (COC), polymethylmethacrylate (PMMA), polycarbonate (PC), polystyrene (PS), polyoxymethylene (POM), perfluoralkoxy (PFA), polyvinylchloride (PVC), polypropylene (PP), polyethylene terephthalate (PET), polyetheretherketone (PEEK), polyamide (PA), polysulfone (PSU), or polyvinylidene fluoride (PVDF) may be used. In addition, as the valve material V1, a phase change material that exists in a solid state at room temperature may be used. The phase change material may be wax. When heated, wax changes into a liquid and a volume thereof expands. Examples of the wax are paraffin wax, microcrystalline wax, synthetic wax, and natural wax. The phase change material may be a gel or a thermoplastic resin. Polyacrylamide, polyacrylates, polymethacrylates, or polyvinylamides may be used as the gel. A plurality of fine exthothermic particles that absorb electromagnetic wave energy and emit heat may be dispersed in the valve material V1. The fine exthothermic particles may have an average particle size of about 1 nm to about 100 μm to freely pass through the fine channel C having a depth of about 0.1 mm and a width of about 1 mm. Also, the fine exthothermic particles may have an exthothermic property, and thus, when electromagnetic wave energy is supplied by, for example, exposure to laser light, a temperature of fine exthothermic particles increases rapidly, and thus, the fine exthothermic particles may homogeneously disperse in wax. To obtain such a property, each of the fine exthothermic particles may have a core including a metallic component and a hydrophobic surface structure. For example, the fine exthothermic particles may each have a molecular structure in which a plurality of surfactants are bound to and cover a Fe-core. The fine exthothermic particles may be preserved in a dispersion state in a carrier oil. The carrier oil may also be hydrophobic to allow the fine exthothermic particles having a hydrophobic surface structure to be homogeneously dispersed. The carrier oil with the fine exthothermic particles dispersed therein is mixed with a molten phase change material, and the resultant mixture is loaded into the channel C and solidified to clog the channel C. The fine exthothermic particles are not limited to the polymer particles presented as an example, and quantum dots or magnetic beads may also be used. In addition, the fine exthothermic particles may be, for example, a fine metal oxide, such as $Al_2O_3$, $TiO_2$, $Ta_2O_3$, $Fe_2O_3$, $Fe_3O_4$, or, $HfO_2$. In addition, no fine exthothermic particles may be necessarily included in the normally closed valve, and according to another embodiment of the present invention, the normally closed valve may be a phase change material without any fine exthothermic particles.

Hereinafter, a method of enriching and separating a target cell by using the microfluidic apparatus 1, according to an embodiment of the present invention, will be described in detail. In the present embodiment, blood containing circulating tumor cells is used as a sample.

[Preparation]: Blood (for example, about 5 mL) containing circulating tumor cells as target cells and fine beads (for example, about $1\times10^8$ or more) with an antibody that specifically connects to an antigen of the target cell are loaded into a sample chamber 310. In addition, appropriately selected DGM is loaded into the separation chamber 200.

DGM may be, for example, Ficoll, Percoll, polysaccharide, NaCl solution, or the like. White blood cells and circulating tumor cells have similar physical properties, and accordingly, when they are centrifuged based on a density gradient, the white blood cells and circulating tumor cells are isolated in an identical layer. Accordingly, according to the present embodiment, fine beads bind to circulating tumor cells and thus induce a density difference from white blood cells, thereby allowing the separation of the tumor cells only from blood. Fine beads may be, for example, melamine particles, and a density thereof may be, for example, about 1.57 g/cm$^3$, which is greater than the density of biological particles in blood, that is, about 1.05 to 1.1 g/cm$^3$.

[Discharging of plasma]: The specific binding of fine beads and a target cell may depend on an antigen-antibody binding described above. Blood may contain various kinds of proteins and such proteins may prohibit the specific binding between the fine beads and the target cell. For example, binding between the fine beads and the target cell may be prevented when a protein that has a structure similar to that of an antigen is bound to a surface marker of a target cell in advance. In addition, binding between the fine beads and the target cell may be prevented when a protein that has a structure similar to that of an antibody binds to a ligand of the fine beads. As such, proteins in blood prevent the generation of a target cell-fine beads complex, thereby lowering the enrichment efficiency of the target cell. To prevent the decrease in enrichment efficiency, proteins in the sample may be removed from the sample before the fine beads are mixed with the sample.

In this case, the microfluidic apparatus 1 is rotated at a rotation rate of about 1000 to 8000 rpm, for example, about 3000 rpm for about 5 minutes. By doing so, the blood in the sample chamber 310 may be divided into a plurality of layers based on a density difference. A red blood cell layer containing the heaviest red blood cell is located farthest away in the radius direction from the rotation center RC. Then, a target layer, including a white blood cell and a target cell, and a plasma layer, which is an upper material layer, are sequentially located closer to the rotation center RC. Since proteins in blood are lighter than blood corpuscles, the proteins are located in the plasma layer. When the microfluidic apparatus 1 is stopped from rotating, an electromagnetic wave, for example, a laser beam is transmitted to the discharge valve 333 to change the discharge valve 333 into an open state. Then, when the microfluidic apparatus 1 is rotated again, plasma is discharged to the waste chamber 330 (according to the embodiment illustrated in FIG. 8, to the first chamber 100) due to a centrifugal force. In this process, all or at least a portion of blood proteins, which prevents the binding between a target cell and fine beads, may be discharged together with the plasma to the waste chamber 330. When the discharge valve 333 is implemented as the combination of the normally closed valve and the normally open, the discharge valve 333 is changed to a blocking state after the plasma is discharged.

[Formation of target cell-fine beads complex]: The microfluidic apparatus 1 is rotated in clockwise and counterclockwise directions for a predetermined period of time to bring fine beads in contact with target cells, thereby attaching the fine beads to the target cells. By doing so, a target material is formed in the sample chamber 110.

[Transportation of fluid]: After the sample valve 331 is open by transmitting thereon an electromagnetic wave, for example, a laser beam, a fluid housed in the sample chamber 310 is transported to the separation chamber 320 housing DGM due to a centrifugal force.

[Separation of target material based on a density gradient in the separation chamber 320]: The microfluidic apparatus 1 is rotated for about 10 minutes for example, at 4000 rpm. Therefore, a plurality of layers, which are distinguished from each other according to a density gradient of materials included in a sample, are formed in the separation chamber 320. For example, a sample is divided into a DGM layer, a red blood cell layer, a white blood cell layer, and a plasma layer in the separation chamber 320. Due to the binding between target cells and fine beads, the density of the complex is the highest, and accordingly, the target cell may be separated in the form of the complex with the fine beads bound thereto from the white blood cell layer, and may be located in the lowest layer of the separation chamber 320, that is, the farthest layer from the rotation center RC in the radius direction, and the DGM layer, the red blood cell layer, the white blood cell layer, and the plasma layer are sequentially located closer to the rotation center RC.

[Recovering of the complex]: Since the separation valve 332 is open, the first fluid including the complex located in the bottom most layer of the separation chamber 320 together with the DGM is transported to the target chamber 70. Once the transportation of the complex is completed, the separation valve 332 is closed. When the transportation of the first fluid to the target chamber 70 is completed, the separation valve 332 may be closed. Like this, by closing the separation valve 332 after the first fluid is transported to the target chamber 70, the first fluid may not flow backward into the separation chamber 320 in a process [transportation of the first fluid to the second chamber] to be described below.

[Transportation of the first fluid to the second chamber]: To perform sequential processes, the first fluid in the target chamber 70 is transported to the second chamber 200. To this end, the first valve 91 and the second valve 92 are open, and the microfluidic apparatus 1 is rotated. Then, the second fluid housed in the first chamber 100 is transported to the target chamber 70 through the first channel 81 due to a centrifugal force. By the pressure of the second fluid, the first fluid in the target chamber 70 is transported to the second chamber 200 through the second channel 82. When the fluid levels of the fluid in the first and second chambers 100 and 200 are equal, an equilibrium state is reached in which the fluid does not flow anymore between the first and second chambers 100 and 200. When a normally open valve is used as the second valve 92, the second valve 92 may be converted to a blocking state in the equilibrium state.

[Sequential processes]: By the above described process, the first fluid and the second fluid including the complex and the DGM are housed in the second chamber 200. The first fluid and the second fluid may be transported to the second processing unit 20 to go through sequential processes. The sequential processes may, for example, include extracting specific materials (for example, a nucleic acid and a protein) from the complex and applying additional reactions (for example, a reaction for target cell staining and a reaction for detaching a bead from the complex).

When a fluid that is not mixed with the first fluid is used as the second fluid, or, when a gas is injected into the first channel 81, the first fluid and the second fluid remain as separate layers in the second chamber 200 as illustrated in FIGS. 5 and 6. Therefore, only the first fluid may easily be transported from the second chamber 200 to the second processing unit 20.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A microfluidic apparatus for inducing a fluid to flow due to a centrifugal force, the apparatus comprising:

a target chamber that houses a first fluid;

a first chamber that houses a second fluid and is disposed closer to a rotation center of the microfluidic apparatus in a radial direction than the target chamber, the first chamber being connected to the target chamber by a first channel;

a first valve that controls a flow of the second fluid through the first channel; and a second chamber disposed closer to the rotation center in radial radius direction than the target chamber and connected to the target chamber by a second channel, wherein the first channel is connected to the target chamber at a first location and the second channel is connected to the target chamber at a second location other than the first location, in an initial state, the second fluid in the first chamber has a first fluid level which is higher than a second fluid level of the first fluid in the target chamber from a perspective of the rotation center of the microfluidic device, and when the second fluid in the first chamber is supplied to the target chamber from the first chamber by the centrifugal force, the first fluid is pushed by the second fluid and is transported from the target chamber to the second chamber until the first and second fluids in the first and second chambers, the target chamber, and the first and second channels reach an equilibrium state, wherein fluid levels of fluids in the first chamber and the second chamber are at a third fluid level lower than the first fluid level.

2. The microfluidic apparatus of claim 1, further comprising a second valve that controls the flow of the first fluid through the second channel.

3. The microfluidic apparatus of claim 1, wherein the first fluid and the second fluid are immiscible.

4. The microfluidic apparatus of claim 1, wherein the first channel is filled with a gas.

5. The microfluidic apparatus of claim 1, further comprising a first processing unit that processes a sample, supplies the first fluid including a target material to the target chamber, and discharges the second fluid, wherein the second fluid comprises a waste fluid that is separated from the sample.

6. The microfluidic apparatus of claim 5, further comprising a second processing unit disposed in an outer portion of the microfluidic apparatus and that receives the first fluid from the second chamber.

7. A microfluidic apparatus for inducing a fluid to flow due to a centrifugal force, the apparatus comprising:

a first processing unit for separating a target cell from a sample;

a target chamber disposed in an outer portion of the microfluidic apparatus and that receives a first fluid including the target cell from the first processing unit;

a first chamber that houses a second fluid, is disposed closer to a rotation center of the microfluidic apparatus in a radial direction than the target chamber, and is connected to the target chamber by a first channel;

a second chamber disposed closer to the rotation center than the target chamber and connected to the target chamber by a second channel; and a second processing unit disposed in the outer portion of the microfluidic apparatus and connected to the second chamber, wherein the first channel is connected to the target chamber at a first location and the second channel is connected to the target chamber at a second location other than the first location, and in an initial state, the second fluid in the first chamber has a first fluid level which is higher than a second fluid level of the first fluid in the target chamber from a perspective of the rotation center of the microfluidic device, and when the second fluid in the first chamber is supplied to the target chamber from the first chamber by the centrifugal force, the first fluid is pushed by the second fluid and is transported from the target chamber to the second chamber until fluid levels of fluids in the first chamber and the second chamber become lower than the first fluid.

8. The microfluidic apparatus of claim 7, further comprising a first valve that controls a flow of the second fluid through the first channel.

9. The microfluidic apparatus of claim 7, further comprising a second valve that controls a flow of the first fluid through the second channel.

10. The microfluidic apparatus of claim 7, wherein the first fluid and the second fluid are immiscible.

11. The microfluidic apparatus of claim 7, wherein the first channel is filled with a gas.

12. The microfluidic apparatus of claim 7, wherein the first processing unit comprises a sample chamber in which a complex in which fine beads are bound to the target cell in the sample is formed; and a separation chamber wherein the complex is separated from the sample using a density gradient medium with a density lower than that of the complex and higher than that of other materials in the sample, wherein the first fluid including the complex is provided to the target chamber.

13. The microfluidic apparatus of claim 12, wherein a waste chamber is connected to the sample chamber, and a waste fluid comprising an upper material layer above the target cell in the sample chamber is discharged from the sample chamber to the waste chamber.

14. The microfluidic apparatus of claim 7, wherein the second processing unit receives the first fluid from the second chamber.

15. The microfluidic apparatus of claim 7, wherein the target cell is a circulating tumor cell, a cancer stem cell, or a cancer cell.

* * * * *